United States Patent
Sjunnesson et al.

(10) Patent No.: US 9,427,310 B2
(45) Date of Patent: Aug. 30, 2016

(54) BODY PART SHAPED MOULD AND A METHOD FOR USING SUCH A MOULD

(75) Inventors: Håkan Sjunnesson, Stockholm (SE); Per Hedèn, Stockholm (SE)

(73) Assignee: Novoaim AB, Stockholm (SE)

( * ) Notice: Subject to any disclaimer, the term of this patent is extended or adjusted under 35 U.S.C. 154(b) by 735 days.

(21) Appl. No.: 13/704,499

(22) PCT Filed: Jun. 20, 2011

(86) PCT No.: PCT/SE2011/050804
§ 371 (c)(1),
(2), (4) Date: Dec. 14, 2012

(87) PCT Pub. No.: WO2011/162704
PCT Pub. Date: Dec. 29, 2011

(65) Prior Publication Data
US 2013/0096675 A1    Apr. 18, 2013

(30) Foreign Application Priority Data
Jun. 21, 2010 (SE) .................................... 1050650-9

(51) Int. Cl.
*A61F 2/12* (2006.01)
*A61F 2/50* (2006.01)
*A61F 2/52* (2006.01)

(52) U.S. Cl.
CPC .............. *A61F 2/12* (2013.01); *A61F 2/5046* (2013.01); *A61F 2/52* (2013.01); *A61F 2002/5015* (2013.01); *A61F 2002/5052* (2013.01); *A61F 2002/5081* (2013.01)

(58) Field of Classification Search
CPC .......... A61F 2/12; A61F 2/5046; A61F 2/52; A61F 2002/5015; A61F 2002/5053; A41C 3/148; A41C 3/146
See application file for complete search history.

(56) References Cited

U.S. PATENT DOCUMENTS

| | | |
|---|---|---|
| 4,086,666 A | 5/1978 | Vaskys et al. |
| 5,824,075 A | 10/1998 | Thielbar |
| 6,443,986 B1 * | 9/2002 | Malice, Jr. ................. A61F 2/52 264/222 |
| 6,660,204 B1 | 12/2003 | Clover, Jr. et al. |
| 6,796,875 B1 * | 9/2004 | Placik .................. A41C 3/0092 450/1 |
| 2002/0193878 A1 * | 12/2002 | Bowman ................... A61F 2/52 623/7 |
| 2007/0267131 A1 | 11/2007 | Reitmeter et al. |

* cited by examiner

*Primary Examiner* — Yogendra Gupta
*Assistant Examiner* — Ninh Le
(74) *Attorney, Agent, or Firm* — Blank Rome LLP

(57) ABSTRACT

The invention relates to a body part shaped mold, for example for creating a test breast, a customized bra or a test body part and a method for using such a mold. The mold is characterized in that it is made of a formstable material having a predetermined shape forming at least one cup. The cup is having a breast like appearance or a body part appearance with a specific size and shape and is adapted to be fitted to a patient's chest or corresponding body part, It is also adapted to be filled with a hardening mixture in a cavity formed between the mold and the chest or corresponding body part. An object of the present invention is to make it possible to try out a suitable size and shape of a breast or other body part, before an implantation is made.

10 Claims, 6 Drawing Sheets

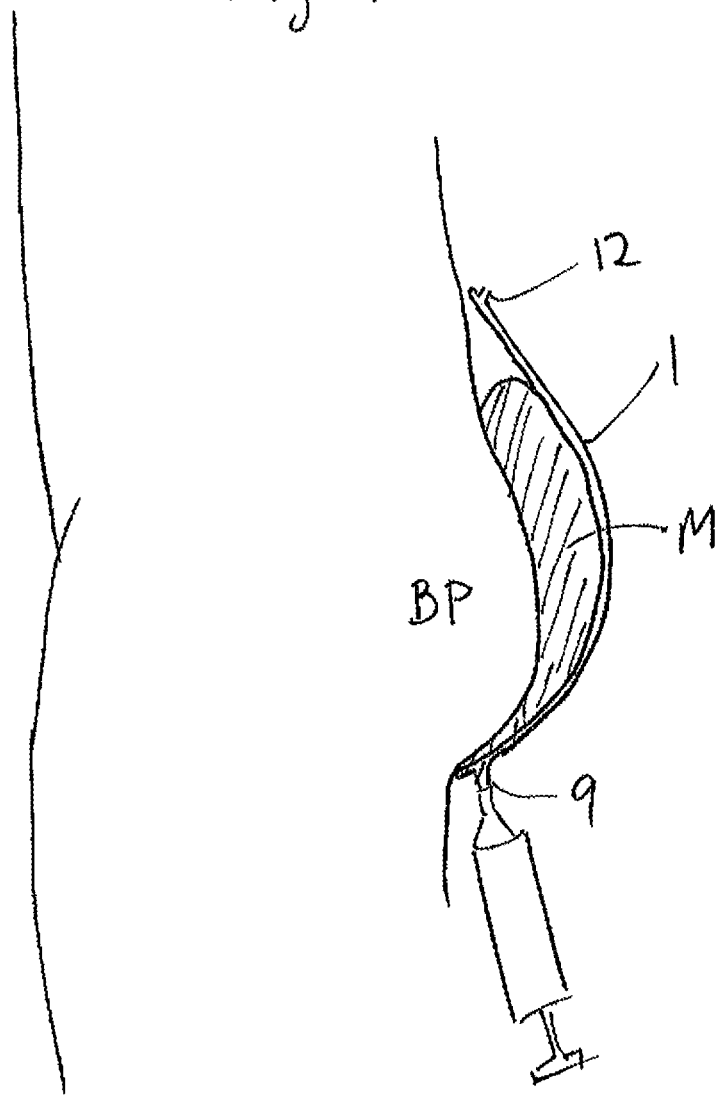

BODY PART SHAPED MOULD AND A METHOD FOR USING SUCH A MOULD

TECHNICAL FIELD

The present invention relates generally to a body part shaped mould and a method for using such a mould, for example to be used before implant surgery.

BACKGROUND ART

Surgical implantation of material in breasts is used both for medical reconstructive and cosmetic purposes. The implants can be made of different materials and have several different shapes and sizes. The size is usually measured in volume or weight of the implanted substance. The shapes of the implants are different due to which surgical operation that is to be performed but in all cases the implants come in different width, height, thickness and profile.

In U.S. Pat. No. 6,796,875B1 a disposable kit for determine the proper size of a surgically implantable breast prosthesis is disclosed. Here a bra-like holder with at least one elastic cup is filled with inflatable flexible bladders of different sizes. The amount of fluid in the bladders can be adjusted by an inflation/deflation device and will form the basis for the decision of volume of the breast prosthesis. This bladder device is impossible to shape. It is also difficult to fit to the existing breast and/or chest. Further, it is not possible to manufacture a specific shape and profile of the breast.

In the above described previous patent the aim is to determine only the size, i.e. the volume of the breast implant. Since the shape of the breast is of such importance for the patient it would be a great advantage if also the shape of the implant can be tried out before surgery. It would be a great advantage if it was possible to sculpture an inexpensive test breast comfortable to wear for a longer period of time.

SUMMARY OF INVENTION

An object of the present invention is to make it possible to try out a suitable size and shape of a breast or other body part, before a breast or other implantation is made. This can be done by a body part shaped mould according to claim 1 and a method according to claim 10. That would make it possible for the patient to, after a visit to the clinic, walk home with a test breast for example and really feel if the size and shape is right.

Additionally it would be possible to use the test breast fitted into a bra instead of surgery or for a longer period of time until the patient has decided to go for surgery.

The invention according to claim 1 is a body part shaped mould. The mould is made of a formstable material having a predetermined shape with at least one cup. The cup is having a breast like appearance or a suitable appearance for other body parts with a specific size and shape and is adapted to be fitted to a patient's chest or corresponding part of the body. It is also adapted to be filled with a hardening mixture in a cavity formed between the mould and the chest/natural breast or natural body part.

By filling a formstable mould with a hardening mixture, the test breast or test body part receives a correct shape and size and it is also custom made after the patient's existing breast and/or shape of the chest or natural body. The mixture will preferably after hardening show a breast-like texture. For example a compressible material retaining its shape after compression, such as a sponge-like material. If the test body part has another texture it is preferred to choose a hardening mixture which after hardening imitates the natural body part.

The cups are reusable and preferably made of a durable material that easily can be sterilised if required.

In further embodiments a first and a second cup may be integrated forming one single mould or be separate from each other forming two separate units. The first and second separate cups may also be joined together with flexible or versatile attachment means.

By using two cups to form the mould a test breast fitting both the right and the left breast of the patient can be sculptured at the same time. By using only one cup it is possible to create only one test breast, for example for patients having one breast removed. If two separate cups flexibly joined together are used as a mould it is possible to adjust each cup in height and in relative position to each other.

In another embodiment the mould is adapted to be fitted to the patient's chest with a bra-like device or an elastic wrap for example. Using a bra-like device of a proper size as a holder for the mould is a simple and convenient solution to hold the mould in place tight to the body.

In a further embodiment the edge of the entire mould or each separate cup is provided with an elastic sealing arrangement preventing the hardening mixture from escaping the mould.

If no sealing is present between the mould and the patient's body, the bra or wrap holding the mould in place must be very tightly stretched. Using a sealing is therefore a solution that makes it more comfortable for the patient during making of the test breasts, customized bra or other test body part.

In other embodiments the hardening mixture comprises material kept in a liquid, viscous, or paste-like state by means of a volatile material or comprises creamed rubber foam formulation containing a foaming agent. Both of these hardening mixtures may harden quickly, preferably without emitting unhealthy gases or creating too much heat. They are preferably also possible to use directly against the skin.

However, for the comfort of the patient it is recommended that a thin layer of plastic or other material is stretched over the patient's chest or corresponding body part before the hardening mixture is inserted.

In another embodiment a bladder is used in order to separate the patient's skin and the hardening mixture, for example if the hardening mixture contains some material, which is not approved to come in contact with human skin. The bladder could be elastically expandable or comprise folds, for example, in order to unfold during the filling with the hardening mixture. Such a bladder could be made of a thermoplastic material, a thermo elastic material, natural rubber or silicon rubber, for example.

The invention further relates to a method using a body part shaped mould according to any of the above described embodiments. The method is having the steps of: choosing a mould with a first size and shape, placing the mould over the existing breast or body part, filling the cavity there between with a hardening mixture creating a custom made test breast, customized bra or test body part, after the mixture is hardened, placing the molded test breast in a bra or placing the molded test body part in a suitable garment or holder. In an embodiment a further step is added to the method, removing the mould after the mixture has hardened.

By using this method the surgeon may quickly and simply create a test breast, a customized bra or a test body part. Since the test part produced by the method are made of an inexpensive, preferably disposable, material it is also possible for the patient to bring the test part home, in order to in peace and quiet determine if the size and shape is right.

The hardening mixture filled in the cavity can be a moldable mixture comprising material kept in a liquid, viscous, or paste-like state by means of a volatile material. The volatile material will be eliminated by causing it to pass into a gaseous phase until the mixture products hardens. The moldable mixture may be any kind of thermo plastic, elastomeric, composite plastic or hardening plastic or mixtures thereof. In one embodiment the basic material in the hardening mixture is a cold hardening silicone.

In one embodiment of the method, the breast shaped or body part shaped mould is chosen from moulds of several sizes and/or shapes.

If the patient is not satisfied with the result it is possible for her to choose another size and/or shape of the mould and the whole procedure is repeated.

BRIEF DESCRIPTION OF DRAWINGS

The invention is now described, by way of example, with reference to the accompanying drawings where.

DESCRIPTION OF EMBODIMENTS

In the following, a detailed description of a body part shaped mould, in this specific example a breast shaped mould and a method using a breast or body part shaped mould is disclosed. All examples herein should be seen as part of the general description and are therefore possible to combine in any way in general terms. Again, individual features of the various embodiments may be combined or exchanged unless such combination or exchange is clearly contradictory to the overall function of the device. Of course a body part shaped mould for any suitable part of the body, like the buttocks, biceps or male chest for example, will be designed, used and functions in a corresponding way as the breast shaped mould. Thus, emphasis is put on the breast shaped mould and the method that are described but the invention covers all types of shaped moulds for different body parts and corresponding methods.

Figure 1A:
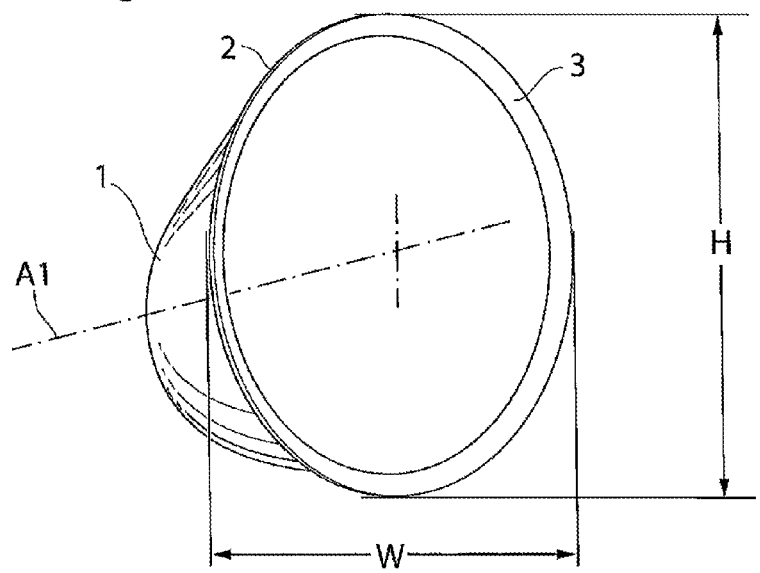
FIG. 1 discloses a cup to be used as a mould according to the invention.
Figure 1B:
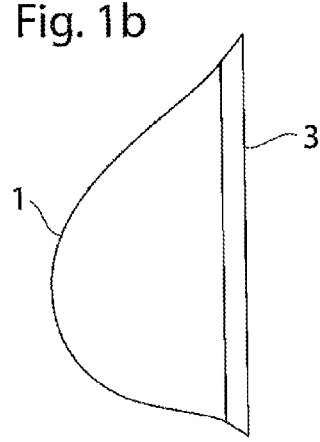
Figure 1C:
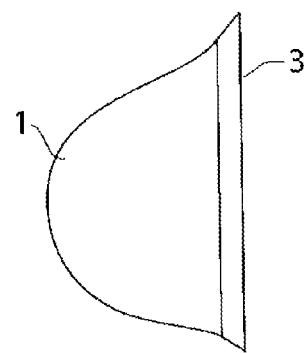

FIG. 1a discloses a cup 1 to be used in a breast shaped mould according to the invention. The cup has a specific width w, height h and shape. The width of a normal breast is usually between 100 and 150 mm. Therefore the cups are available in sizes with a width in that same range 100-150 mm, preferably in steps of 5 mm. The height h and shape of the cups are different and are preshaped in for example anatomical (FIG. 1b) or rounded (FIG. 1c) form. In order to give the patient a great freedom to choose the cups are available in several sizes and shapes, preferably there shall be between 20 and 40 cups available at the clinic creating the test breast.

Figure 1D:
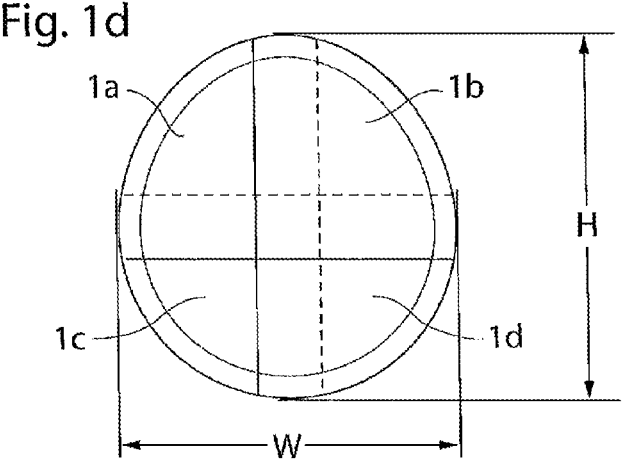

In one embodiment, shown in FIG. 1d, it is also possible to slightly change the width w and height h of the cup 1. Preferably this is done by dividing the cup 1 into at least two, but preferably four or more, formstable parts 1a, 1b, 1c, 1d which are, at least to some extent, overlapping and are displaceable in relation to each other. Depending on how the parts 1a-1d are shaped and how much they are overlapping it is possible to adjust the shape of the entire mould but locking the mould to a formstable and specific size and shape before use.

Preferably the edge 2 of the cup 1 is provided with an elastic sealing arrangement 3 preventing the mixture from escaping the mould. The elastic sealing 3 is formable after the patient's chest and has preferably an extension in a direction essentially parallel and/or transversal to the centre axis A1 of the cup. When using a sealing 3 with a certain extension it provides a soft flexible skirt where the cup 1 presses against the body. Thus, it can easier be tightly shaped after the patient's chest. The sealing 3 can be a single or double seal and is preferably made of silicone or rubber.

Figure 2:
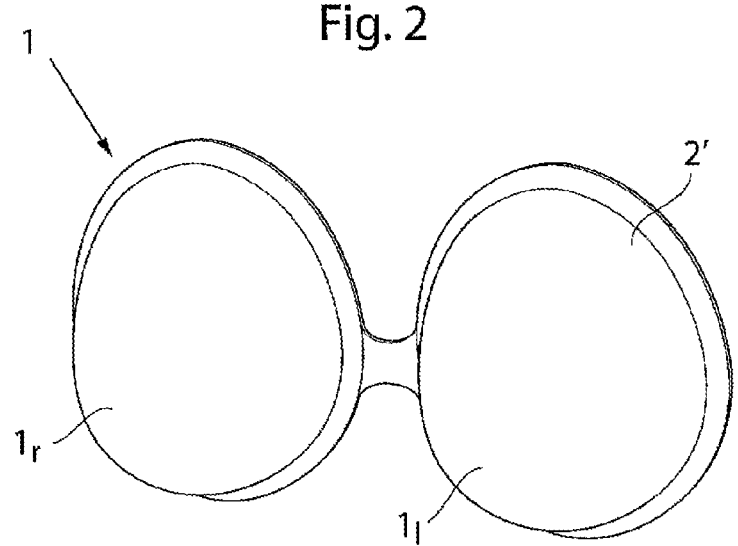
FIG. 2 discloses a mould with first and second cups integrated so that they are forming one single mould, FIG. 3 discloses a mould comprising two separate cups flexibly joined together and placed in a bra, FIG. 4 discloses a side view of a mould in a bra being placed on a patient's chest being filled with expandable/hardening mixture, FIG. 5 discloses a front view of the mould during filling, FIG. 6 discloses a side view of a mould in a bra being placed on a patient's chest being filled with expandable/hardening mixture within a bladder, and FIG. 7 discloses an embodiment of a mould for making a test body part, in the shown case for a buttock.

In FIG. 2 a first and a second cup $1_r$, $1_l$ are used as mould. The first and second cups are integrated so that they are forming one single mould. The single mould can have a flexible part joining the first and second cup. In this embodiment the sealing 3 can be placed around the edge 2 of the entire mould. However it is also possible to use two seals encircling each of the separate cups $1_r$, $1_l$.

Figure 3:
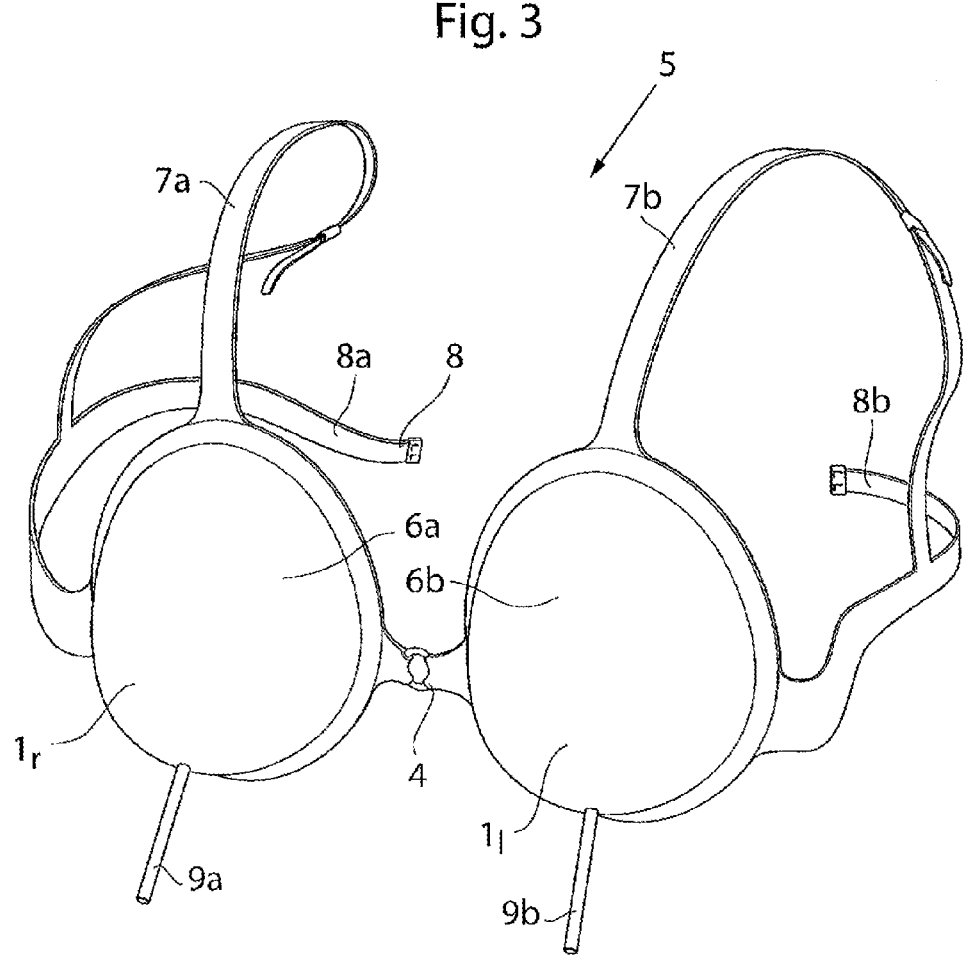

In FIG. 3 it is disclosed a mould comprising two separate, right and left placed cups $1_r$, $1_l$ flexibly joined together by a joint 4 and placed in a bra-like device 5. The bra-like device 5 comprises two cup holders 6a, 6b in which a first and a second adjustable shoulder ribbon 7a, 7b and an adjustable back ribbon 8 are attached. The shoulder ribbons 7a, 7b are adapted to be arranged over each shoulder of the patient. The back ribbon 8 may be one single elastic ribbon or two joinable ribbon parts 8a, 8b, as disclosed in the figure.

The joint 4 joining the two cups $1_r$, $1_l$ is flexible or versatile and can also in one embodiment be openable. The cup holders 6a, 6b can be an outer ring, preferably supporting each cup at its outer edge or a piece of material, preferably elastic, supporting the entire outer surface of the cups $1_r$, $1_l$.

Means 9a, 9b for filling each cup $1_r$, $1_l$ with the hardening mixture M is also attached in each cup. The fillings means 9a, 9b can for example be pipes or a hole stretching thorough the cups $1_r$, $1_l$ and, if necessary, also through the cup holders 6a, 6b. In FIG. 3 one filling means is arranged in each cup, however, it is also possible to use more than one filling means. At least one air outlet 12 is preferably present to release the air inside of the cup while the hardening mixture is filled. It could for example be a pipe or a hole in the upper area of the cup.

Figure 4:
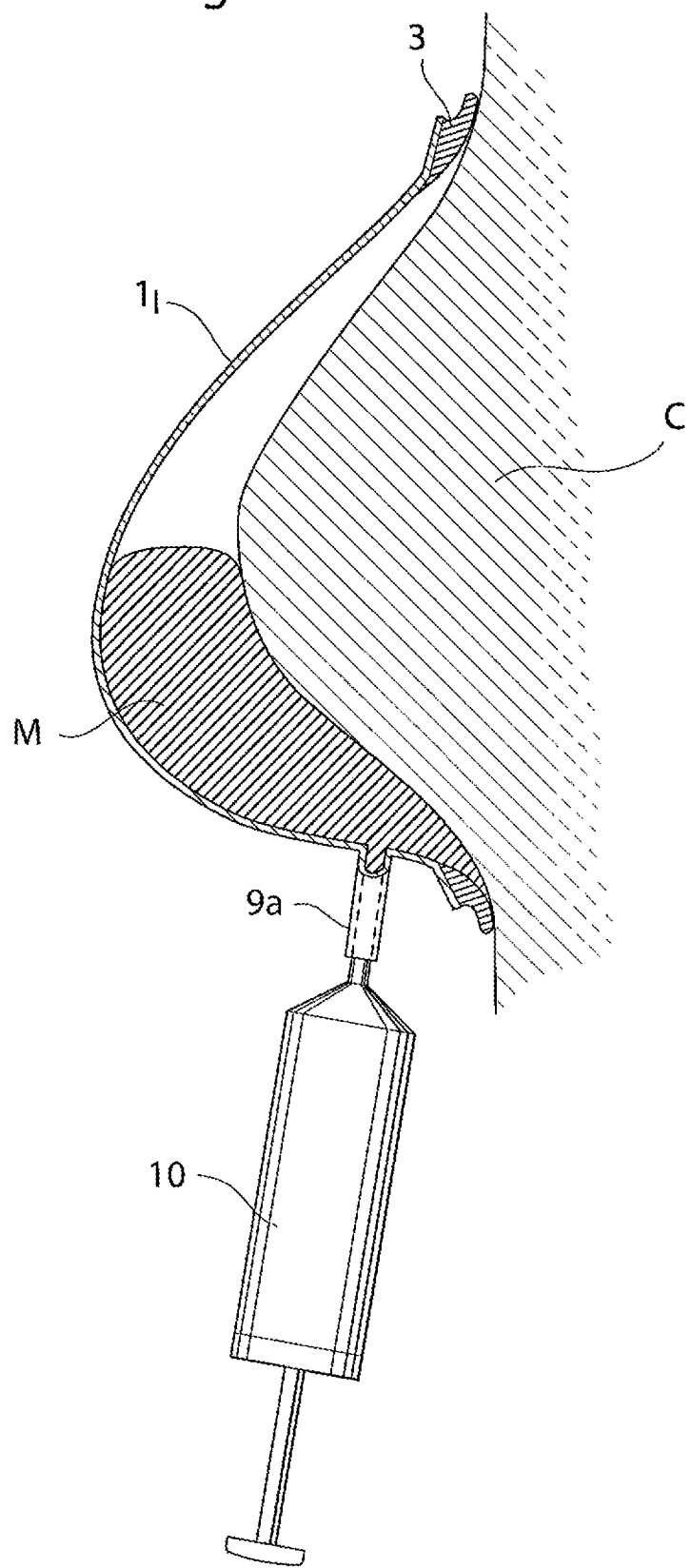
Figure 5:
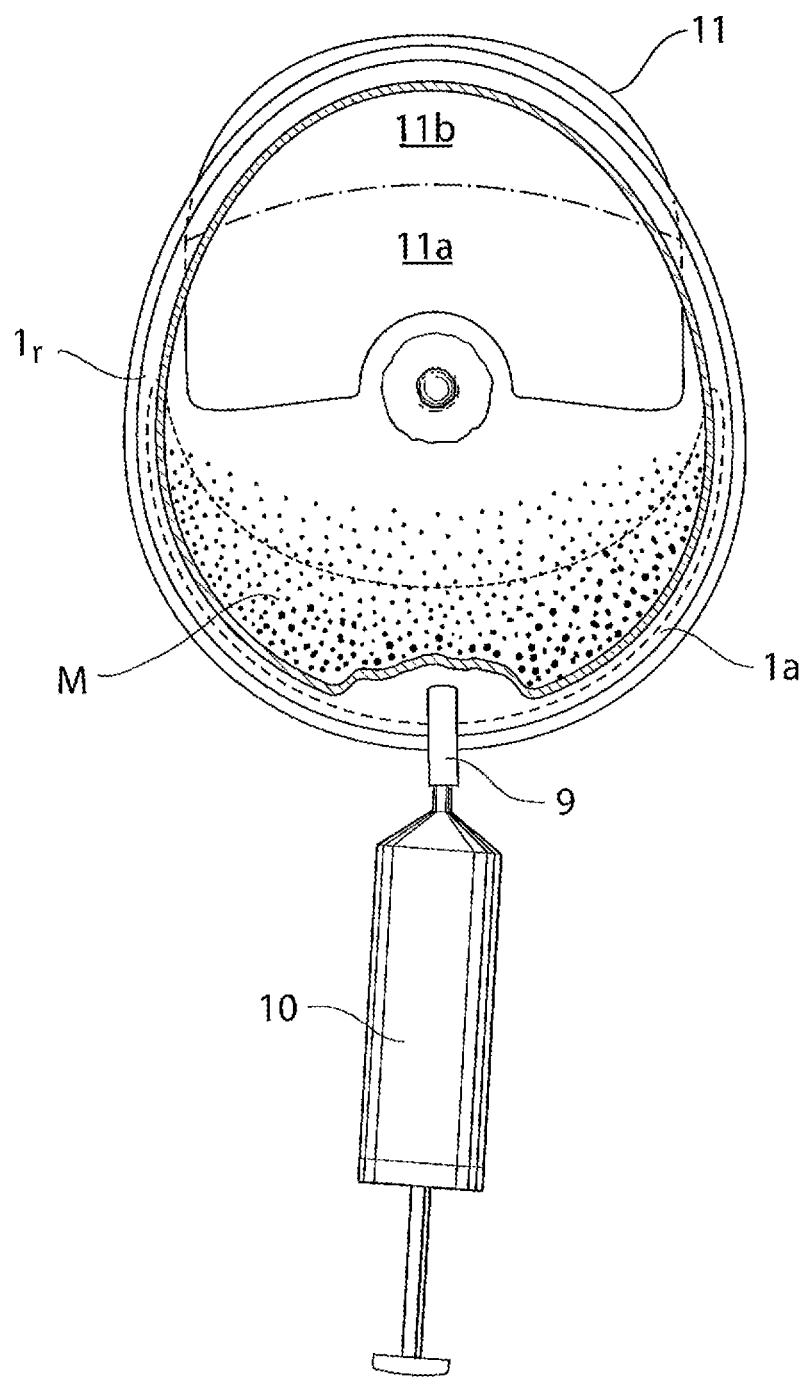

In FIG. 4 it is disclosed a cut through of a side view of a one of the cups 1, and in FIG. 5 a front view of the same cup 1, is disclosed. The cup 1, is placed on a patient's chest C and is filled with the hardening mixture M through the filling means 9a. In this embodiment the hardening mixture M is inserted through the filling means 9a into the cavity between the cup 1, and the chest C. A squirt 10 or similar arrangements may be used to insert the mixture into the cavity. Preferably, the fillings means is arranged under the patent's existing breasts so that the mixture M is pressing the breasts up and slightly in towards the neck part of the patient. However, other placements of the fillings means are possible. In another embodiment a bladder 13 is arranged inside of the cup, preferably in the lower region of the breast or underneath the breast. The bladder 13 is filled via at least one filling means 9 with the hardening mixture M. Any air present inside the bladder 13 may be released through at least one air outlet 12 in the upper region of the bladder 13. Preferably the patient is sitting up during the moulding.

In FIG. 5 an embodiment of the invention is disclosed where the natural breast is lifted into an uplifted position by an adhesive tape 11. A lower part 11a of the tape 11 is adhered to the breast and an upper part 11b is adhered to the chest above the breast. By first adhering the lower part 11b and then lifting in the upper part 11b of the tape 11 before adhering the upper part of the tape to the chest, the breast can be positioned in the uplifted position. When the breast is in the uplifted position the hardening mixture M is inserted under the breast, thus creating the desired shape of the test breast, with the aid of the natural breast. The natural breast is, in this embodiment, forming the upper part of the test breast.

When the mixture M has hardened into a formstable test breast, preferably with a breast-like texture retaining its shape after compression, it is possible to remove the test breast from the mould and place it in the patient's personal bra. However, it is also possible to keep the test breast in the mould using the whole mould as a breast shaping detail.

The test breast might also be used in a custom made bra to be sold as a separate object. The bra is preferably at least one size larger than the normal bra size of the person. In order to securely lock the test breast in the correct position in relation to the patient's normal breasts it can be put in a separate pocket in the bra.

As disclosed in FIGS. 4 and 5 the method of filling the mould may also have the steps of:
- placing the mould over the existing breast, filling the cavity therein with a moldable hardening mixture comprising material kept in a liquid, viscous, or paste-like state by means of a volatile material, and then
- eliminating at least one of the volatile materials by causing it to pass into a gaseous phase until the mixture material hardens.

Figure 6:
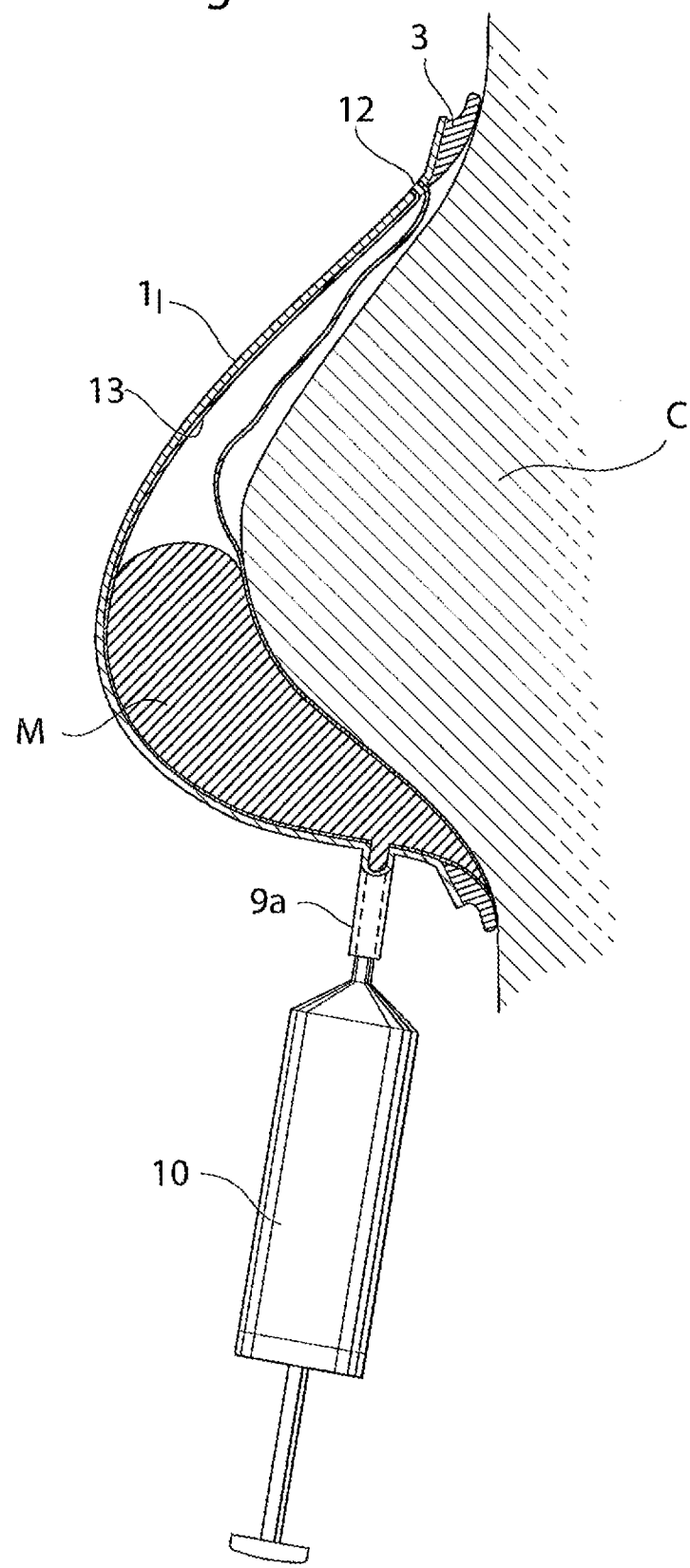

In case of using a hardening mixture which is not suitable to be in contact with the human skin, a bladder 13 could be arranged in between the cup 1 and the breast/chest of the patient. A possible embodiment is shown in FIG. 6. The bladder 13 could be freely positioned, attached to the inside of the cup 1 or attached to the breast/chest of the patient.

In FIG. 7 an embodiment of the present invention is shown. A body part shaped mould 1 is disclosed, in this specific case it is a mould for the buttock, which is provided over a body part BP. The method for using a body part shaped mould corresponds to the method for the breast shaped mould, as described above.

The mixture of viscous hardening material used for moulding a test breast may comprise: a binder comprising at least one of the following material: an elastomeric material, a plastic material, a mixture of these two types of materials, or a mixture of a plurality of materials of the same type; a filler; and a volatile material.

The elastomeric material may be any elastomer capable of being placed in solution, suspension, or emulsion, e.g., natural rubber, reticulated or not, a butyl, nitrile, or chlorinated rubber, a polyisobutylene, an ethylene/propylene rubber, a styrene-butadiene or styrene-isoprene copolymer, a latex, a polyurethane, a silicone, an isobutylene/isopropylene copolymer, or a Thiokol (polysulfide polymer).

The plastic material may be any type of plastic capable of being placed in solution, suspension, or emulsion in conventional solvents, e.g., a polyamide, a polyurethane, an acrylic, a cellulosic, a glycerophthalic, epoxy or vinylic material.

The filler may be mineral or synthetic vegetable or organic material. The preferred grain size is between 0.1 and 30 mm. The filler may be resiliently compressible, in which case it consists preferably or scrap polyurethane foam, rubber powder, polyethylene foam or cork powder. The filler may, of course, be a mixture of different materials.

The preferred volatile material may be a solvent made of plastic and/or elastomeric materials, more particularly an aliphatic, aromatic, halogenated, ketonic product, with an ether, ester or alcohol function. It may have a plurality of functions and may have a straight, branched or cyclic chain. It is conceivable to use a mixture of solvents in order to lower the boiling point by means of an azeotrope.

The solvent selected will preferably have a boiling point of less than 150° C., preferably less than 80° C. (at normal pressure). The vapor tension should also be such as to allow easy evaporation.

The moldable mixture introduced into the cavity may also contain polystyrene, or a polystyrene copolymer, placed in solution in a solvent or a mixture of solvents, capable of passing into a gaseous phase under close-to-normal pressure and/or temperature conditions, i.e., at atmospheric pressure (760 mm Hg) and at an ambient temperature of about 20-25° C.

The invention claimed is:

1. A method for using a body part shaped mould in order to make a test breast or a test body part for a patient before an implant surgery, comprising the steps of:
    choosing a mould cup made of a formstable material having a predetermined first size and shape and that is reusable, made of a durable material that can be sterilized, and configured to be placed in a bra-like device or elastic wrap fitted to the patient's chest, patient's existing breast, or corresponding body part;
    placing the mould cup into the bra-like device or elastic wrap and over the patient's chest, or the patient's existing breast, or the corresponding body part;
    arranging a bladder between the mould cup and the patient's chest, the patient's existing breast, or the corresponding body part;
    filling the bladder with a hardening mixture creating a custom made test breast, custom made bra, or custom made test body part;
    after the hardening mixture is hardened, placing the custom made test body part in a bra, an elastic wrap, or a garment.

2. A method according to claim 1, wherein the mould cup is removed after the hardening mixture has hardened.

3. A method according to claim 1, wherein the body part shaped mould is chosen from moulds of several sizes and/or shapes.

4. A method according to claim 1, wherein a first and a second cups are used as moulds.

5. A method according to claim 4, wherein a first and a second cups are used as mould and the first and second cups are integrated so that they are forming one single mould.

6. A method according to claim 4, wherein the first and second cups are joined together by a flexible or versatile joint.

7. A method according to claim 1, wherein an edge of the entire mould or each separate cup is provided with an elastic sealing arrangement preventing the hardening mixture from escaping the mould.

8. A method according to claim 1, wherein the hardening mixture consists of products kept in a liquid, viscous, or paste-like state by a volatile product.

9. A method according to claim 1, wherein the hardening mixture consists of creamed rubber foam formulation containing a foaming agent.

10. A method according to claim 1, wherein the step of placing the mould cup into the bra-like device or elastic wrap comprises placing the mould cup into a cup holder of the bra-like device or elastic wrap.

* * * * *